United States Patent
Littarru et al.

(10) Patent No.: US 7,303,921 B2
(45) Date of Patent: Dec. 4, 2007

(54) METHOD TO ASSAY COENZYME $Q_{10}$ IN BLOOD PLASMA OR BLOOD SERUM

(76) Inventors: Gian Paolo Littarru, Institute of Biochemistry, University of Ancona Via Ranieri, 60131 Ancona (IT); Fabrizo Mosca, Via Aldo Moro 3 bis, 60030 Monsano (AN) (IT); Daniele Fattorini, Institute of Biology & Genetics, University of Ancona, Via Ranieri, 60131 Ancona (IT); Stefano Bompadre, Institute of Microbiology & Biomedical Sciences, University of Ancona, Via Ranieri, 60131 Ancona (IT)

(*) Notice: Subject to any disclaimer, the term of this patent is extended or adjusted under 35 U.S.C. 154(b) by 551 days.

(21) Appl. No.: 10/444,535

(22) Filed: May 23, 2003

(65) Prior Publication Data

US 2004/0033553 A1 Feb. 19, 2004

Related U.S. Application Data

(60) Provisional application No. 60/382,943, filed on May 23, 2002.

(51) Int. Cl.
*G01N 30/02* (2006.01)
(52) U.S. Cl. .......................... 436/161; 435/4
(58) Field of Classification Search ............ None
See application file for complete search history.

(56) References Cited

OTHER PUBLICATIONS

Hiroshima et al. "Rapid method for determination of ubiquinone in biological materials by high-performance liquid chromatography", Bitamin, 1985, 59(9), 457-63, Abstract.*
Tomasetti, et al., Distribution of antioxidants among blood components and lipoproteins: significance of lipids/$CoQ_{10}$ ration as a possible marker of increased risk for atherosclerosis. BioFactors, 9, 231-240 (1999).
Littarru, et al., Metabolic and diagnostic implications of human blood $Q_{10}$ levels, in Biomedical and Clinical Aspects of Coenzyme Q vol. VI, (eds. K. Folkers, G.P. Littarru, T. Yamagami), Elsevier North Holland, pp. 167-178 (1991).
Alleva, et al., Oxidation of LDL and their subfractions: kinetic aspects and $CoQ_{10}$ content. Molec Asp Med, 18 s015-s112 (1997).
Mortenson, et al., Dose-related decrease of serum coenzyme $Q_{10}$ during treatment with HMG-CoA reductase inhibitors. Molec Asp Med, 18, s137-s144 (1997).

(Continued)

*Primary Examiner*—Yelena G. Gakh
(74) *Attorney, Agent, or Firm*—McCarter & English, LLP (57) ABSTRACT

A method is described for determining $CoQ_{10}$ concentrations in plasma samples. $CoQ_{10}$ in the plasma sample is oxidized by treating the sample with an oxidizing agent having a redox potential higher than the redox potential of $CoQ_{10}$, such as, for example, para-benzoquinone. Following oxidation of the $CoQ_{10}$, the $CoQ_{10}$ in the plasma sample is extracted with an alcohol, such as, for example, 1-propanol. The alcohol extract is analyzed using direct injection into the HPLC apparatus. This method achieves a rapid, accurate analysis of plasma $CoQ_{10}$ levels, which can be used for monitoring the bioavailability of orally administered $CoQ_{10}$ used as a food supplement or as an adjunctive therapy.

10 Claims, 4 Drawing Sheets

OTHER PUBLICATIONS

Lang, et al., Quantitative determination of vitamin E and oxidized and reduced coenzyme Q by high-performance liquid chromatography with in-line ultraviolet and electrochemical detection, J Chromatogr, 385, 109-117 (1987).

Finckh, et al., High-performance liquid chromatography-coulometric electrochemical detection of ubiquinol 10, ubiquinone 10, carotenoids and tocopherols in neonatal plasma, in Methods in Enzymology, vol. 299 (Lester Packer Ed.), pp. 341-348, Academic Press, San Diego (1999).

Podda, et al., Sensitive high-performance liquid chromatography techniques for simultaneous determination of tocopherols, tocotrienols, ubiquinols and ubiquinones in biological samples in Methods in Enzymology, vol. 299, (Lester Packer Ed.), pp. 330-341, Academic Press, San Diego (1999).

Finckh, et al., Monitoring of ubiquinol 10, ubiquinone 10, carotenoids and tocopherols in neonatal plasma microsamples using high-performance liquid chromatography with coulometric electrochemical detection. Anal. Biochem, 232, 210-216 (1985).

Okamoto, et al., Determination of reduced and total ubiquinones in biological materials by liquid chromatography with electrochemical detection, J. Chromatogr, 430, 11-19 (1988).

Grossi, et al., Improved high-performance liquid chromatographic method for the determination of coenzyme $Q_{10}$ in plasma. J. Chromatogr., 593, 217-226 (1988).

Edlund, P.O., Determination of coenzyme $CoQ_{10}$, $\alpha$-tocopherol and cholesterol in biological samples by coupled-column liquid chromatography with coulometric and ultraviolet detection. J. Chromatogr, 415, 87-97 (1988).

Lagendijk, et al., Measurement of the ratio between the reduced and oxidized forms of coenzyme Q10 in human plasma as a possible marker of oxidative stress, J. Lipid Res, 37, 67-75 (1996).

Yamashita, et al., Simultaneous detection of ubiquinol and ubiquinone in human plasma as a marker of oxidative stress, Anal. Biochem, 250, 66-73 (1997).

\* cited by examiner

METHOD TO ASSAY COENZYME $Q_{10}$ IN BLOOD PLASMA OR BLOOD SERUM

This application claims the benefit of U.S. Provisional Application Ser. No. 60/382,943 filed on May 23, 2002.

BACKGROUND OF THE INVENTION

Coenzyme $Q_{10}$ (2,3 dimethyl-5-methyl-6-decaprenyl benzoquinone) ("$CoQ_{10}$") levels in whole blood and plasma have been the subject of much inquiry as described, for example, in Tomasetti, M., Alleva, R., Solenghi, M. D., Littarru, G. P., Distribution of antioxidants among blood components and lipoproteins: significance of lipids/$CoQ_{10}$ ratio as a possible marker of increased risk for atherosclerosis. *BioFactors*, 9, 231-240 (1999), the entire content of which is incorporated herein by reference. It is likely that plasma concentrations of $CoQ_{10}$ reflect an overall metabolic demand, as discussed in Littarru, G. P., Lippa, S., Oradei, A., Fiorini, R. M., Mazzanti, L., Metabolic and diagnostic implications of human blood $CoQ_{10}$ levels, in Biomedical and Clinical Aspects of Coenzyme Q vol. VI, (eds. K. Folkers, G. P. Littarru, T. Yamagami), Elsevier North Holland, pp. 167-178 (1991), the entire content of which is incorporated herein by reference. In addition, together with other lipophilic antioxidants, $CoQ_{10}$ plays an intrinsic role in protecting circulating lipoproteins against oxidative damage. Therefore, the concentration of $CoQ_{10}$ in lipoproteins and blood plasma could be of clinical importance regarding oxidative stress and antioxidant defense. Increased levels of $CoQ_{10}$ enhance its antioxidant protection, even though the potential to act as an antioxidant in vivo probably depends not only on total $CoQ_{10}$ concentration, but also on its redox status. The content of $CoQ_{10}$ in single classes of lipoproteins has been found to be strictly correlated with $CoQ_{10}$ plasma concentration. Previous reports have shown that the LDL-cholesterol/$CoQ_{10}$ ratio significantly correlates with the total-cholesterol/HDL-cholesterol ratio which is usually considered a risk factor for atherosclerosis as described, for example in Alleva, R., Tomasetti, M., Bompadre, S., Littarru, G. P., Oxidation of LDL and their subfractions: kinetic aspects and $CoQ_{10}$ content. *Molec Asp Med*, 18, s105-s112 (1997), the entire content of which is incorporated herein by reference. Some effective hypocholesterolemic agents, namely the statins, also lower plasma $CoQ_{10}$ concentrations, owing to the common biosynthetic pathway of cholesterol and the isoprenoide side chain of coenzyme Q as described, for example, in Mortensen, S. A., Leth, A., Agner, E., Rohde, M., Dose-related decrease of serum coenzyme $Q_{10}$ during treatment with HMG-CoA reductase inhibitors. *Molec Asp Med*, 18, s137-s144 (1997), the entire content of which is incorporated herein by reference. Therefore, it would be desirable to have an effective, reliable, fast method to measure $CoQ_{10}$ concentrations in blood plasma or blood serum to monitor the $CoQ_{10}$ levels in patients receiving hypocholesterolemic agents.

$CoQ_{10}$ is used as a food supplement or as an adjunctive therapy in several diseases and the blood plasma or blood serum levels achieved upon oral administration of CoQ10 can correlate with clinical efficacy. Tests of blood plasma or blood serum levels of $CoQ_{10}$ are useful for monitoring the bioavailability of orally administered coenzyme $Q_{10}$.

Several methods have been described for assaying either total $CoQ_{10}$ or the reduced (ubiquinol-10, $CoQ_{10}H_2$) and oxidized (ubiquinone-10) forms in blood plasma, and several of these methods are described in the following references, the entire contents of each of which are incorporated herein by reference: Lang, J. K, Packer, L., Quantitative determination of vitamin E and oxidized and reduced coenzyme Q by high-performance liquid chromatography with in-line ultraviolet and electrochemical detection, *J Chromatogr*, 385, 109-117 (1987); Finckh, B., Kontush, A., Commentz, J., Hubner, C., Burdeleski, M., Kohlschutter, A., High-performance liquid chromatography-coulometric electrochemical detection of ubiquinol 10, ubiquinone 10, carotenoids and tocopherols in neonatal plasma, in Methods in Enzymology, Vol 299, (Lester Packer Ed.), pp. 341-348, Academic Press, San Diego (1999); Podda, M., Weber, C., Traber, M. G., Milbradt, R., Packer, L., Sensitive high-performance liquid chromatography techniques for simultaneous determination of tocopherols, tocotrienols, ubiquinols and ubiquinones in biological samples in Methods in Enzymology, Vol 299, (Lester Packer Ed.), pp. 330-341, Academic Press, San Diego (1999); Finckh, B., Kontush, A., Commentz, J., Hubner, C., Burdeleski, M., Kohlschutter, A. Monitoring of ubiquinol 10, ubiquinone 10, carotenoids and tocopherols in neonatal plasma microsamples using high-performance liquid chromatography with coulometric electrochemical detection. *Anal. Biochem*, 232, 210-216 (1985); Okamoto, T., Fukunaga, Y., Ida, Y., Kishi, T., Determination of reduced and total ubiquinones in biological materials by liquid chromatography with electrochemical detection, *J. Chromatogr*, 430, 11-19 (1988); Grossi, G., Bargossi, A. M., Fiorella, P. L., Piazzi, S. Improved high-performance liquid chromatographic method for the determination of coenzyme $Q_{10}$ in plasma. *J. Chromatogr.*, 593, 217-226 (1988); Edlund, P. O., Determination of coenzyme $CoQ_{10}$, α-tocopherol and cholesterol in biological samples by coupled-column liquid chromatography with coulometric and ultraviolet detection. *J. Chromatogr*, 425, 87-97 (1988); Lagendijk, J., Ubbink, J. B., Vermaak, W. J., Measurement of the ratio between the reduced and oxidized forms of coenzyme Q10 in human plasma as a possible marker of oxidative stress, *J. Lipid Res*, 37, 67-75 (1996); Yamashita, S., Yamamoto, Y., Simultaneous detection of ubiquinol and ubiquinone in human plasma as a marker of oxidative stress, *Anal. Biochem*, 250, 66-73 (1997). As used herein, ubiquinol means reduced $CoQ_{10}$ and ubiquinone means oxidized $CoQ_{10}$.

The previous methods of analyzing blood plasma to assay the concentration of $CoQ_{10}$ have several disadvantages. Prior methods require that the $CoQ_{10}$ be extracted from the plasma, followed by drying, which concentrates the extract. Losses in $CoQ_{10}$ can occur during the drying and concentration step. In addition, these methods analyze the oxidized form of $CoQ_{10}$, while most of the $CoQ_{10}$ in the plasma is in the reduced form. These methods rely on oxidation of the $CoQ_{10}$ during the extraction procedure. UV methods for assaying $CoQ_{10}$ usually quantify the oxidized coenzyme at 275 nm. It is commonly assumed that $CoQ_{10}$ is completely oxidized during the extraction and HPLC procedure, but this is not necessarily the case when the sample is fresh and the reduced form of $CoQ_{10}$ largely predominates. Accordingly, these methods can result in underestimates of $CoQ_{10}$ concentration if all of the $CoQ_{10}$ is not oxidized.

The present invention is directed to a new, simplified method for evaluating total $CoQ_{10}$ in blood plasma or blood serum. The method of the present invention results in reduced time and cost for the analysis of $CoQ_{10}$ in plasma or serum as compared to prior methods, and provides more accurate results.

DETAILED DESCRIPTION OF THE INVENTION

The present invention relates to a method to assay the concentration of $CoQ_{10}$ in blood plasma or blood serum. The sample of blood plasma or blood serum is treated with an oxidizing agent having a redox potential higher than the redox potential of $CoQ_{10}$, followed by extraction with an alcohol and direct injection of the alcohol extract into a High Performance Liquid Chromatography ("HPLC") apparatus.

In a preferred embodiment of the method, the $CoQ_{10}$ in the plasma or serum sample is oxidized by adding para-benzoquinone as an oxidizing agent. Extraction is performed using an alcohol, preferably n-propanol. The extract is then assayed by direct injection of the propanol extract into the HPLC apparatus without bringing the extract to dryness. The method can be conducted on fresh plasma or serum samples since $CoQ_{10}$ present in the sample is oxidized prior to propanol extraction.

The method may be performed using an oxidizing agent other than benzoquinone. For example, other oxidizing agents having a redox potential higher than the ubiquinone/ubiquinol couple may be used in the method. Also, the extraction of the oxidized $CoQ_{10}$ in the plasma or serum sample may be performed using any appropriate alcohol known to those skilled in the art. For example, 1-propanol, butanol or pentanol may be used for the extraction of the oxidized $CoQ_{10}$.

A particularly preferred embodiment of the present method is set forth in the Example below. It should be understood that the description set forth below is not intended to limit the invention in any way, and those skilled in the art will readily understand that modifications to the reagents, equipment or other parameters set forth below can be made without departing from the spirit or scope of the invention. Results obtained using the method on various samples are also described below.

EXAMPLE

Materials and Methods

Reagents. R.S. type methanol and n-propanol were used (obtained from Carlo Erba, Rodano, Milan, Italy). Ethanol was R.S. plus grade (obtained from Carlo Erba, Rodano, Milan, Italy). Benzoquinone was obtained from Sigma (St Louis, Mo., USA). Lithium perchlorate was obtained from Aldrich (Steinheim, Germany).

Solutions for the ECD (electrochemical detection) chosen as a reference method were filtered through a Nylon 66 membrane, 0.2 µm×47 mm (Supelco, Bellafonte, Pa., USA) and degassed. Pure Coenzyme $Q_{10}$ standard was obtained from Kaneka (Osaka, Japan). Standard solutions were in ethanol.

Samples. Blood was drawn from the cubital vein of laboratory staff, after informed consent, and anti-coagulated with lithium heparin. Plasma obtained after centrifugation at 4,000 g for 15 min., at 4° C. was used fresh, or after storage at −80° C. for the day-to-day precision assay.

In order to check the stability of total $CoQ_{10}$ in plasma, aliquots of 3 different samples were kept for 3 days at 4° C., room temperature (22° C.) and at −20° C. respectively.

High Performance Liquid Chromatography. The HPLC apparatus consisted of a Beckman System pump model 126, a detector model 166 (Beckman Instruments, San Ramon, Calif., USA) and an injector equipped with a 2001 µl loop (Rheodyne 7725i obtained from Supelco, Milano, Italy). The column was a Supelcosil LC 18 (obtained from Supelco, Milano, Italy) 25 cm×0.46 cm i.d. 5µ, precolumn LC 18S, 2 cm. (obtained from Supelco, Milano, Italy). An in line filter A-701 (obtained from Upchurch Scientific, Inc., Oak Harbor, Wash., USA) was placed between the injector and the precolumn. The photodiode array detector for the UV spectrum analysis of the $CoQ_{10}$ peak was a SPD-M (Shimadzu, Tokyo).

Description of the Analysis. 200 µl of a blood plasma sample were supplemented with 50 µl of a 1,4 benzoquinone solution (2 mg/ml) in a test tube and vortexed for 10 seconds. After 10 minutes, 1 ml of n-propanol was added. The test tube was vortexed for 10 seconds and centrifuged at 10,000 rpm for 2 minutes in order to spin down the protein precipitate. 200 µl of the supernatant were injected into the HPLC. The supernatant, placed in a capped test tube, was stable for up to three days when kept at 22° C. Mobile phase was constituted by ethanol-methanol (65%-35%) and the flux was 1 ml/min. UV detection was performed at 275 nm.

200 µl of different concentrations of pure oxidized $CoQ_{10}$ were injected as standards. Working solutions of the standards were in propanol:water (5:1), i.e. the same propanol: water ratio as for the samples. Peak area analysis was performed by a Beckman Gold Data System (DOS version).

Coulometric analysis. Coulometric analysis of $CoQ_{10}$ was performed according to a standard procedure described in Alleva, R., Tomasetti, M., Bompadre, S., Littarru, G. P., Oxidation of LDL and their subfractions: kinetic aspects and $CoQ_{10}$ content. *Molec Asp Med*, 18, s105-s112 (1997). Ubiquinol/ubiquinone separation was performed on an ODS reversed phase column (Supelcosil LC18, 15×4.6 mm i.d. 3 µm, Supelco, Milano, Italy) using a mobile phase constituted by 50 mM sodium perchlorate in methanol:ethanol (80:20), at flow rate of 1 ml/min. A Coulochem II, model 5200 electrochemical detector (ESA, Bedford, Mass., USA), with the analytical cell set at −0.5 V and +0.35 V was used to detect the oxidized and reduced forms of $CoQ_{10}$.

Recovery, Accuracy and Precision. Recovery of $CoQ_{10}$ was based on a comparison between the peaks obtained by spiking samples with increasing concentrations of oxidized $CoQ_{10}$ and the corresponding peaks of the standard. Recovery was documented at 3 concentrations (1.16, 2.32, and 3.48 µM) with triplicate determinations for each concentration. Intra-assay accuracy and precision were determined using 4 samples, the value of which had been certified by a reference ECD method; each level was assayed 5 times for the intra-assay accuracy and precision test. Inter-assay accuracy and precision were determined over a two-month period using a quality control sample (n=21).

Results

Figure 1A:
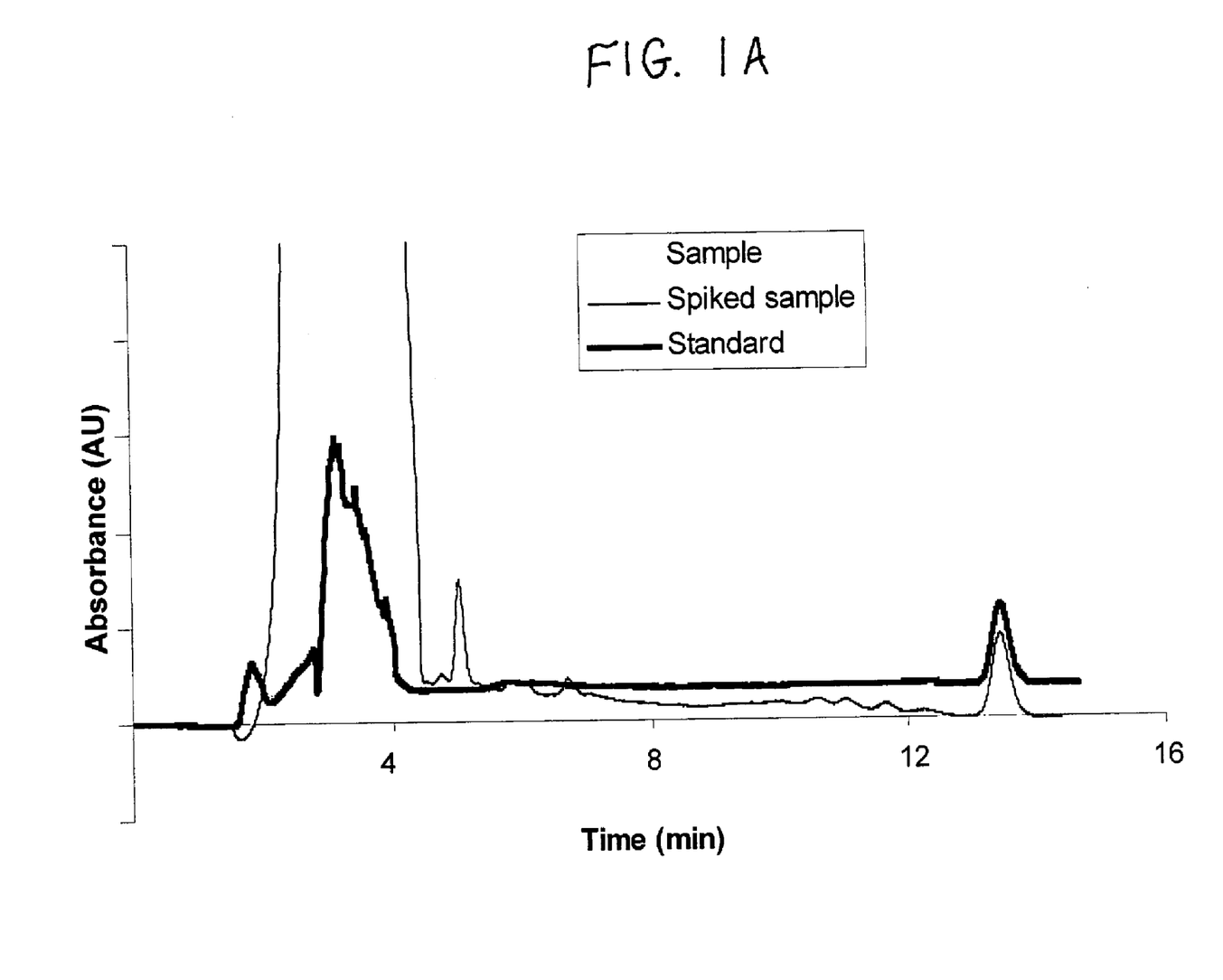
FIG. 1A shows a typical chromatogram of a plasma sample, before and after spiking with a known amount of standard. A typical chromatogram of the standard alone is also shown.
Figure 1B:
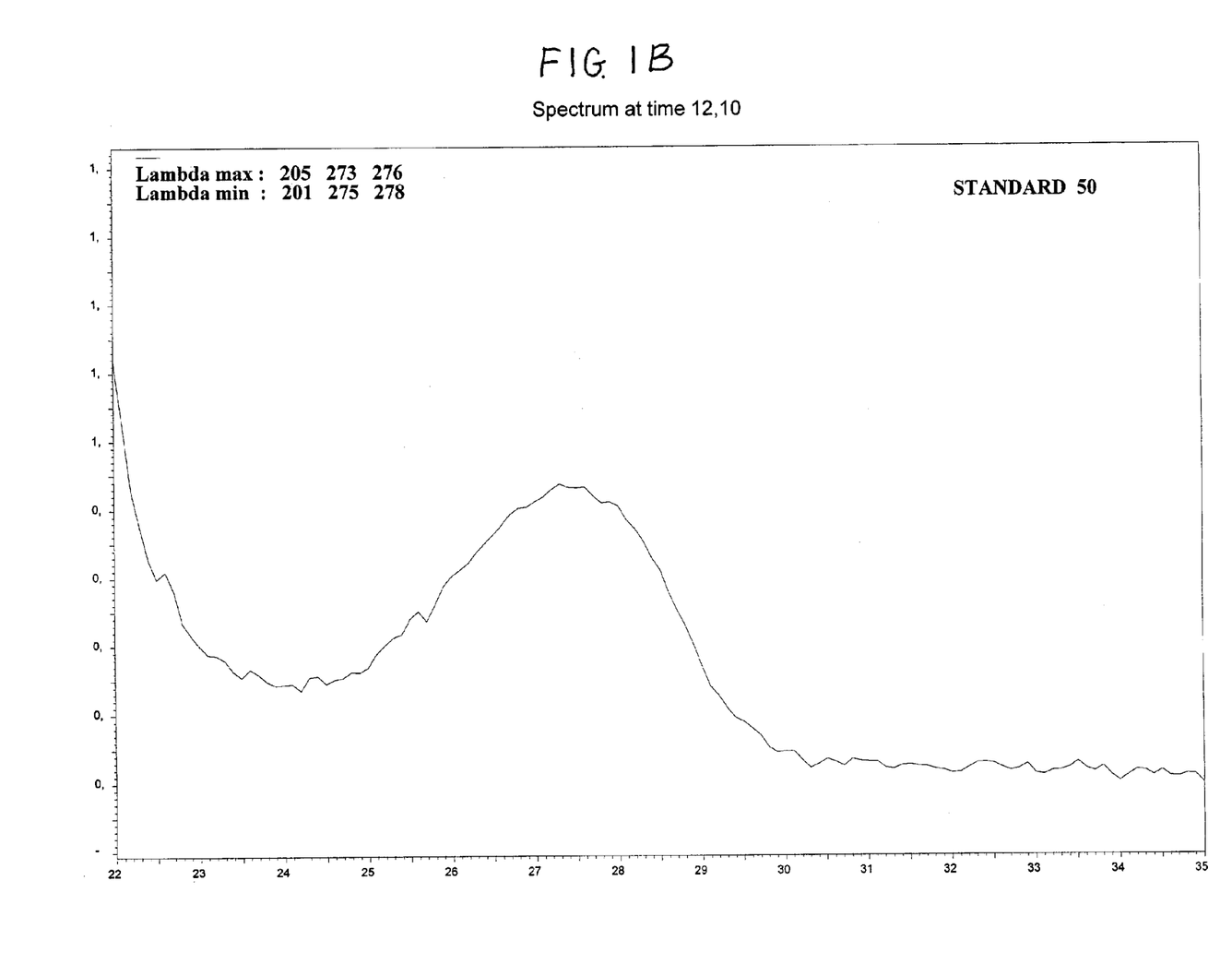
FIG. 1B shows a diode array analysis of the peak of a standard of $CoQ_{10}$ (50 ng).
Figure 1C:
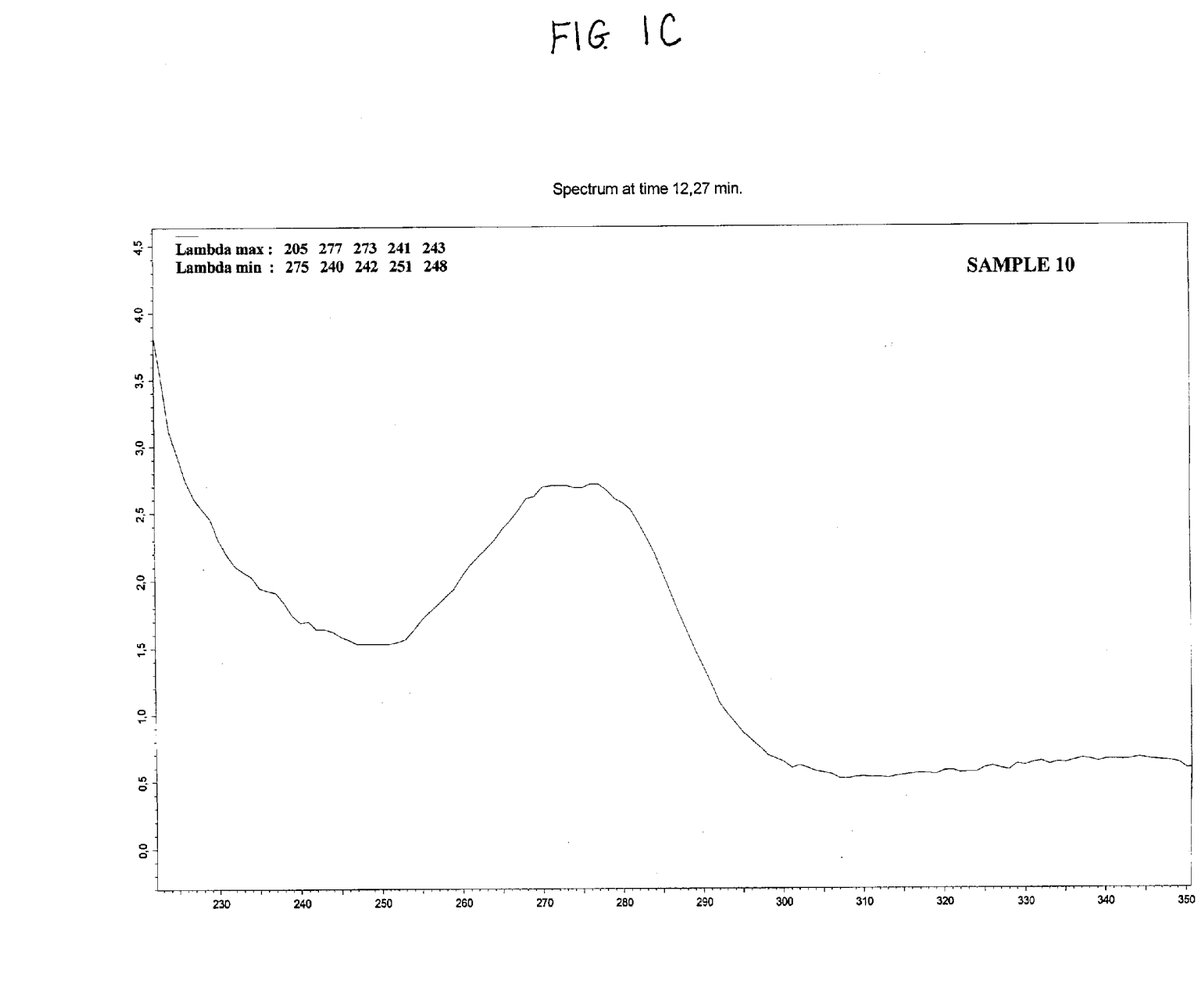
FIG. 1C shows a diode array analysis of the peak obtained on a plasma sample analyzed by the method of the present invention.

Chromatography and recovery. Typical, representative chromatograms of both a standard and a plasma sample are shown in FIG. 1A. Diode array analysis of the peak with the same retention time as the $CoQ_{10}$ standard is also shown in FIGS. 1B and 1C. Spiking of a sample containing an initial concentration of 0.29 µM with 1.16, 2.32 or 3.48 µM $CoQ_{10}$ yield a recovery of 96.3, 98.1 and 98.5% as shown in Table 1.

TABLE 1

Recovery of exogenous $CoQ_{10}$ added to a plasma sample

| | Measured (pM) | Recovery |
|---|---|---|
| Basal concentration | 0.29 | |
| Spiking with $CoQ_{10}$ 1.16 µM | 1.40 | 96.3% |
| Spiking with $CoQ_{10}$ 2.32 µM | 2.56 | 98.1% |
| Spiking with $CoQ_{10}$ 3.48 µM | 3.72 | 98.5% |

Calibration curves. Calibration curves constructed using propanol/water solutions of pure $CoQ_{10}$ as described in the Materials and Methods section above showed linearity over a concentration range of 7.9-579 nM, corresponding to a concentration of 47.4-3474 nM $CoQ_{10}$ in plasma. Correlation coefficients ($r^2$) for 20 calibration curves obtained over a two month period ranged from 0.98 to 0.999 The limit of quantitation was 0.037 µM (1.23 nmoles in column) with a precision of 10.52%.

Accuracy and precision. Within run (intra-assay) precision (CV %) and accuracy, determined as deviation from nominal values, appear in Table 2. Four samples with different, decreasing concentrations of total $CoQ_{10}$, having a nominal value previously determined by the electrochemical detection method chosen as reference, were analysed five times each. As shown in Table 2, CV % becomes consistently higher than 5 only for samples less than 0.06 µM.

Normal plasma values of $CoQ_{10}$ typically range between 0.75 and 0.98 µM. Deviation from nominal values was never higher than 4.7%.

TABLE 2

Within run accuracy and precision

| Expected concentration (nM) | Measured concentration (nM) | Deviation % | C.V. % |
|---|---|---|---|
| 894 | 911 | 1.9% | 1.6% |
| 447 | 432 | −3.4% | 5.3% |
| 178 | 170 | −4.7% | 5.7% |
| 36 | 37 | 2.6% | 10.5% |

Day-to-day precision, conducted over a two month period, is summarized in Table 3. For values corresponding to normal plasma concentrations, accuracy and precision were comparable to that obtained in the intra-assay conditions.

TABLE 3

Day to day accuracy and precision test

| | |
|---|---|
| Nominal concentration of sample (µM) | 0.81 |
| Mean of 21 measurements (µM) | 0.80 |
| % deviation from nominal value | 0.7 |
| C.V. % | 2.16 |

Figure 2:
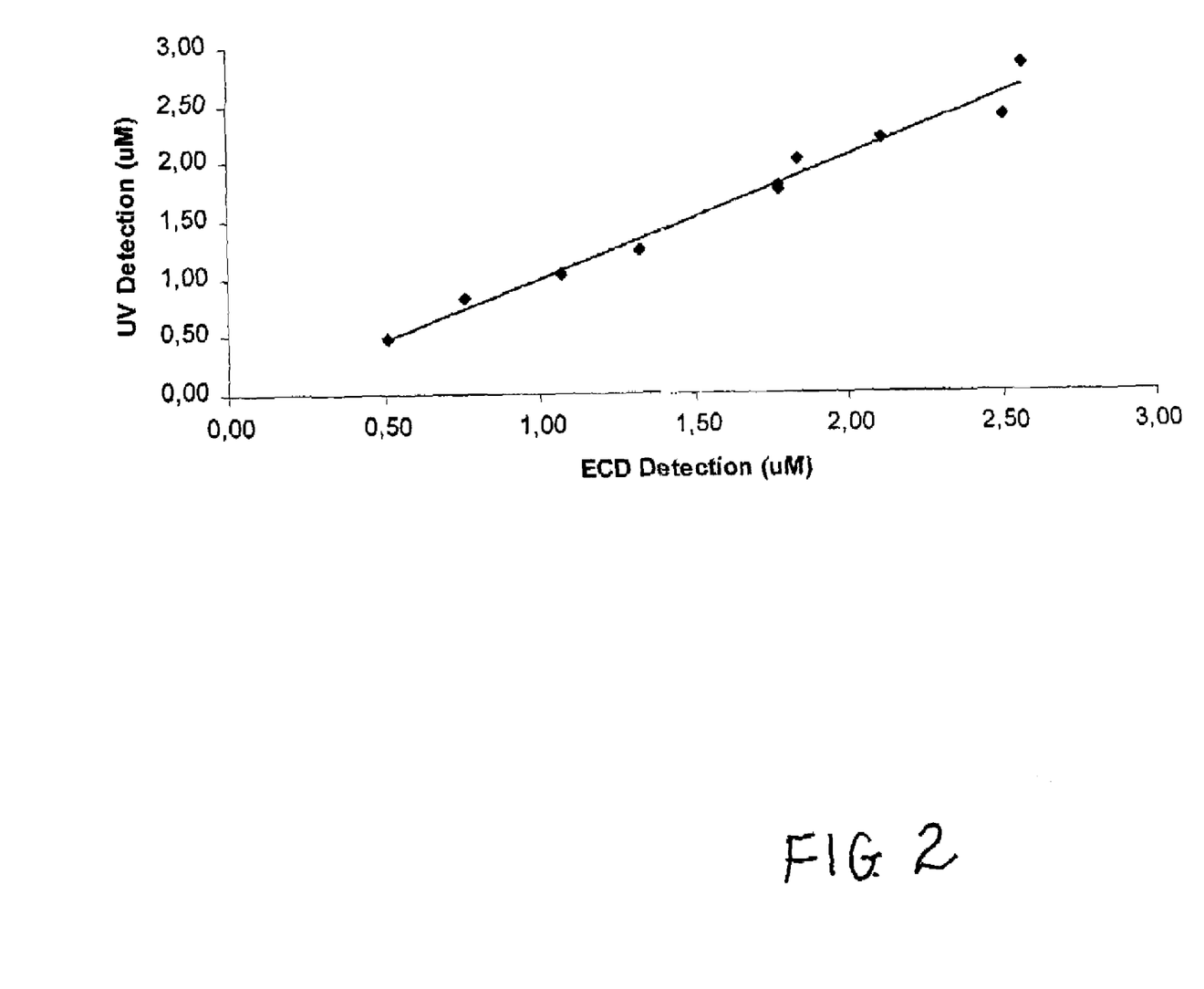
FIG. 2 shows a linear correlation between the results obtained by analysis of a sample for $CoQ_{10}$ using a reference electrochemical detection method and the method of the present invention.

Comparison with the ECD method. Ten samples were analysed, in parallel, both by the electrochemical method (ECD) and by the method of the present invention (UV), and the results are shown in Table 4. These samples were chosen on the basis of their different levels of total $CoQ_{10}$ and different extent of reduction. Correlation between the results of total $CoQ_{10}$ obtained by the two methods appears in FIG. 2.

TABLE 4

Results from a group of samples analysed by electrochemical (ECD) and by UV detection

| | ECD Detection | | | | UV Detection | |
|---|---|---|---|---|---|---|
| Sample | Oxidized $CoQ_{10}$ (µM) | Reduced $CoQ_{10}$ (µM) | Total $CoQ_{10}$ (µM) | Red/Tot (%) | Total $CoQ_{10}$ (µM) | % Variation |
| A | 0.95 | 1.62 | 2.57 | 63.09% | 2.84 | 10.27% |
| B | 1.47 | 0.30 | 1.78 | 17.12% | 1.75 | −1.44% |
| C | 0.02 | 0.74 | 0.76 | 97.36% | 0.83 | 9.44% |
| D | 2.01 | 0.10 | 2.11 | 4.80% | 2.18 | 3.50% |
| E | 0.30 | 1.02 | 1.32 | 77.56% | 1.22 | −7.51% |
| F | 0.45 | 0.05 | 0.51 | 10.76% | 0.48 | −6.62% |
| G | 2.11 | 0.40 | 2.51 | 15.92% | 2.37 | −5.53% |
| H | 0.15 | 1.69 | 1.84 | 92.03% | 2.00 | 8.89% |
| I | 0.58 | 0.49 | 1.07 | 45.91% | 1.03 | −3.38% |
| L | 0.94 | 0.84 | 1.78 | 47.03% | 1.79 | 0.71% |

Stability. The results obtained on 3 different samples stored for 1,2 or 3 days at different temperatures are shown in Table 5. Total $CoQ_{10}$ was practically stable for at least three days even when kept at room temperature.

TABLE 5

Stability of $CoQ_{10}$ values at different storage conditions and times

| | | Time after blood withdrawal (hours) | | | | | | | |
|---|---|---|---|---|---|---|---|---|---|
| | | 1 h. | | 24 h. | | 27/34 48 h. | | 72 h. | |
| Sample | Storage conditions | Mean μM | St. Dev. | Mean μM | St. Dev. | Mean μM | St. Dev. | Mean μM | St. Dev. |
| A | Control | 1.73 ± 0.05 | | | | | | | |
| | Room Temp. | | | 1.91 ± 0.03 | | 1.81 ± 0.00 | | 1.93 ± 0.03 | |
| | 0-4° C. | | | 1.97 ± 0.03 | | 1.82 ± 0.11 | | 1.82 ± 0.16 | |
| | −20° C. | | | 1.84 ± 0.05 | | 1.91 ± 0.08 | | 1.97 ± 0.05 | |
| B | Control | 1.06 ± 0.03 | | | | | | | |
| | Room Temp. | | | 1.11 ± 0.04 | | 1.05 ± 0.02 | | 1.02 ± 0.03 | |
| | 0-4° C. | | | 1.06 ± 0.05 | | 1.03 ± 0.08 | | 1.11 ± 0.03 | |
| | −20° C. | | | 1.14 ± 0.06 | | 1.00 ± 0.00 | | 1.09 ± 0.03 | |
| C | Control | 2.68 ± 0.11 | | | | | | | |
| | Room Temp. | | | 2.72 ± 0.12 | | 2.80 ± 0.11 | | 2.83 ± 0.09 | |
| | 0-4° C. | | | 2.81 ± 0.15 | | 2.78 ± 0.01 | | 2.94 ± 0.07 | |
| | −20° C. | | | 2.84 ± 0.11 | | 2.80 ± 0.08 | | 2.93 ± 0.08 | |

Discussion of Results. Prior methods for evaluating $CoQ_{10}$ in plasma and biological tissues are based on alcohol-hexane extraction; the extract is brought to dryness and injected into the HPLC apparatus, where $CoQ_{10}$ is usually revealed and quantified at 275 nm or by electrochemical detection. An internal standard, such as $CoQ_8$ or $CoQ_9$, is often added to the sample before extraction, in order to quantify a recovery. In all previously described methods, the organic solvent extract is brought to dryness and therefore concentrated before injection into the HPLC.

In the present method the sample is only diluted with propanol and then injected into the HPLC. Direct injection of the propanol extract also makes the procedure particularly simple and fast. Prior oxidation of reduced $CoQ_{10}$ with para-benzoquinone eliminates the possibility of underestimating total $CoQ_{10}$ in fresh samples. In fact fresh samples contain almost exclusively reduced $CoQ_{10}$ and the usual extraction procedures are often not sufficient to completely oxidize ubiquinol. On the other hand UV detection at 275 only reveals ubiquinone. The chromatographic features and the diode array analysis of the peak show a selective separation of $CoQ_{10}$, with no superimposed peaks. Reproducibility of the method is shown by a CV below 2% for samples having normal values of plasma $CoQ_{10}$ and about 5% for samples having a quarter of the normal amount.

The rather low retention time for $CoQ_{10}$, under the chromatographic conditions makes the analysis fast enough and the peak does not overlap with any other components, as shown by similar values obtained using the ECD method and by the diode array analysis of the peak.

The efficiency of $CoQ_{10}$ extraction by the method of the present invention appears to be very satisfactory as the addition of 1, 2 or 3 μg of $CoQ_{10}$ to a sample leads to a 96.3-98.5% quantitative recovery (see Table 4) which makes the use of an internal standard unnecessary. This is in agreement with data from Edlund's work (Edlund, P. O., Determination of coenzyme $CoQ_{10}$, α-tocopherol and cholesterol in biological samples by coupled-column liquid chromatography with coulometric and ultraviolet detection. *J. Chromatogr,* 425, 87-97 (1988)) where it appears that a dilution of the sample with n-propanol (1:4) leads to a 100% recovery.

Correlation with the reference ECD method gave an r=0.98 (p<0.0001) as shown in Table 4. The data of Table 4 also show the efficiency of the method in properly quantifying different concentrations of $CoQ_{10}$ and different extents of reduction. Fresh samples have their $CoQ_{10}$ almost completely reduced, see Lagendijk, J., Ubbink, J. B., Vermaak, W. J., Measurement of the ratio between the reduced and oxidized forms of coenzyme Q10 in human plasma as a possible marker of oxidative stress, *J. Lipid Res,* 37, 67-75 (1996); Yamashita, S., Yamamoto, Y., Simultaneous detection of ubiquinol and ubiquinone in human plasma as a marker of oxidative stress, *Anal. Biochem,* 250, 66-73 (1997). Therefore, the testing described above also included some samples which had been frozen and thawed several times, where $CoQ_{10}$ was partially or almost completely oxidised. It is evident that the extent of reduction of $CoQ_{10}$ in the sample does not affect the final result.

For practical reasons the propanol extract can be kept in the refrigerator up to 3 days before injection into the HPLC. Several samples were checked by analysing them 1 hour, 1, 2 and 4 days after drawing the blood, keeping the samples at −20° C., 0-4° C., or +22° C. (room temperature) and the results, as far as total $CoQ_{10}$ was concerned, were the same for the same sample whether kept at different temperatures or for different lengths of time (presumably only the reduced/oxidised $CoQ_{10}$ ratio changed). There was no need to add any stabilizing agent to the sample.

The data reported above demonstrates that the method of the present invention is simple and reliable, it minimizes sample handling, allows a quantitative recovery of $CoQ_{10}$ and it does not need an internal standard. Data not reported show that it is adaptable to semi-automated procedures and can be applied to tissue homogenates.

As will be recognized by those of ordinary skill in the art based on the teachings herein, numerous changes and modifications may be made to the above-described methods without departing from its spirit or scope as defined in the appended claims. Accordingly, this detailed description of preferred embodiments is to be taken in an illustrative, as opposed to a limiting sense.

We claim:

1. A method for determining the concentration of $CoQ_{10}$ in blood plasma or blood serum, comprising the steps of:
   (a) obtaining a sample of blood plasma or blood serum from a human;
   (b) treating the sample with 1,4-benzoquinone to oxidize the $CoQ_{10}$ in the sample;
   (c) extracting the oxidized $CoQ_{10}$ from the sample using an alcohol; and
   (d) following extraction of the $CoQ_{10}$, analyzing the alcohol extract using High Pressure Liquid Chromatography to determine the concentration of $CoQ_{10}$ in the alcohol extract.

2. The method of claim 1, wherein the alcohol is selected from the group consisting of n-propanol, butanol and pentanol.

3. The method of claim 1, wherein the alcohol is 1-propanol.

4. The method of claim 1, wherein the High Pressure Liquid Chromatography is performed using ultraviolet detection.

5. A method for determining the concentration of $CoQ_{10}$ in blood plasma or blood serum, comprising the steps of:
   (a) obtaining a sample of blood plasma or blood serum from a human;
   (b) depositing an aliquot of the sample in a container;
   (c) adding to the sample in the container a sufficient volume of 1,4 benzoquinone to oxidize $CoQ_{10}$ in the sample;
   (d) vortexing the sample containing the oxidizing agent;
   (e) allowing the vortexed sample to stand for a sufficient period of time for the 1,4 benzoquinone to oxidize $CoQ_{10}$ contained in the sample;
   (f) adding an alcohol to the sample to extract the oxidized $CoQ_{10}$ from the sample;
   (g) vortexing the sample containing the alcohol;
   (h) centrifuging the sample containing the alcohol to spin down any protein precipitate;
   (i) removing an aliquot of the supernatant from the centrifuged sample and analyzing the aliquot of supernatant using High Pressure Liquid Chromatography to determine the concentration of $CoQ_{10}$ in the sample.

6. The method of claim 5, wherein the alcohol is selected from the group consisting of n-propanol, butanol and pentanol.

7. The method of claim 5, wherein the alcohol is 1-propanol.

8. The method of claim 5, wherein the High Pressure Liquid Chromatography is performed using ultraviolet detection.

9. A method for determining the concentration of $CoQ_{10}$ in blood plasma or blood serum, comprising the steps of:
   (a) obtaining a sample of blood plasma or blood serum from a human and depositing 200 µl of the sample in a test tube;
   (b) adding 50 µl of 1,4-benzoquinone solution to the sample contained in the test tube, wherein the 1,4-benzoquinone solution contains 2 mg 1,4-benzoquinone/ml solution, and vortexing the sample and 1,4-benzoquinone for about 10 seconds;
   (c) allowing the test tube containing the vortexed sample to stand for about 10 minutes;
   (d) adding 1 ml of 1-propanol to the test tube and vortexing the resulting the sample and the alcohoi in the test tube for about 10 seconds;
   (e) centrifuging the test tube at about 10,000 rpm for about 2 minutes;
   (f) removing 200 µl of supernatant from the test tube and injecting the supernatant into a High Performance Liquid Chromatography apparatus to determine the concentration of $CoQ_{10}$ in the sample.

10. The method of claim 9, wherein the High Pressure Liquid Chromatography is performed using ultraviolet detection.

* * * * *